(12) United States Patent
Mastrobuono et al.

(10) Patent No.: US 11,182,577 B1
(45) Date of Patent: Nov. 23, 2021

(54) SCANNING LABELS TO EXTRACT AND STORE STRUCTURED INFORMATION

(71) Applicant: Titan School Solutions, Inc., Irvine, CA (US)

(72) Inventors: Karim Mastrobuono, San Clemente, CA (US); Tianfu Dai, Newport Beach, CA (US)

(73) Assignee: Titan School Solutions, Inc., Wilmington, NC (US)

( * ) Notice: Subject to any disclaimer, the term of this patent is extended or adjusted under 35 U.S.C. 154(b) by 0 days.

(21) Appl. No.: 16/906,769

(22) Filed: Jun. 19, 2020

Related U.S. Application Data

(60) Provisional application No. 62/864,718, filed on Jun. 21, 2019.

(51) Int. Cl.
  *G06K 7/14* (2006.01)
  *G16H 20/60* (2018.01)
(52) U.S. Cl.
  CPC ........... *G06K 7/1417* (2013.01); *G16H 20/60* (2018.01)
(58) Field of Classification Search
  CPC .............................. G06K 7/1417; G16H 20/60

USPC ......................................................... 235/494
See application file for complete search history.

(56) References Cited

U.S. PATENT DOCUMENTS

| | | | | |
|---|---|---|---|---|
| 2012/0087551 | A1* | 4/2012 | Bhagwan | G06K 9/00255 382/118 |
| 2013/0273509 | A1* | 10/2013 | Mutti | G09B 19/0092 434/127 |

OTHER PUBLICATIONS

Firebase, Text Recognition, printed Jun. 20, 2019.
Github, hermitdave. Frequencywords, printed Jun. 20, 2019.
Github, wolfgarbe, SymSpell, printed Jun. 20, 2019.
Grubert et al., Recognition of Nutrition Facts Labels from Mobile Images, printed Jun. 20, 2019.

* cited by examiner

*Primary Examiner* — Daniel A Hess
(74) *Attorney, Agent, or Firm* — Van Pelt, Yi & James LLP

(57) ABSTRACT

A plurality of image frames is received. A line of text comprising a nutritional ingredient and a corresponding frame-specific quantity is recognized in each of at least a subset of the image frames. A reported quantity for the nutritional ingredient is determined based at least in part on the respective corresponding frame-specific quantities.

15 Claims, 7 Drawing Sheets

| No SIM 📶 11:32 AM 14% 🔋 |  |
|---|---|
| Nutrition Data | |
| Serving | |
| Serving | 42g |
| Nutrition | |
| Calories | 210 |
| Total fat | 5g |
| Saturated fat | 2.5g |
| Trans fat | 0g |
| Total carbs | 24g |
| Sugars | 0g |
| Calcium | 40mg |
| Potassium | 40mg |
| Ingredients | |
| wheat flour | 8 |
| Submit | |
| Reset | |

| No SIM 📶 11:32 AM 14% 🔋 |  |
|---|---|
| Nutrition Data | |
| Ingredient | |
| wheat flour | 8 |
| niacin | 8 |
| reduced iron | 7 |
| palm | 5 |
| enriched flour | 5 |
| soybean | 5 |
| salt | 2 |
| vit | 2 |
| and or canola oil with tbhq for fresh... | 2 |
| vegetable oil | 2 |
| vital | 2 |
| reduced | 2 |
| Submit | |
| Reset | |

SCANNING LABELS TO EXTRACT AND STORE STRUCTURED INFORMATION

CROSS REFERENCE TO OTHER APPLICATIONS

This application claims priority to U.S. Provisional Patent Application No. 62/864,718 entitled SCANNING LABELS TO EXTRACT AND STORE STRUCTURED INFORMATION filed Jun. 21, 2019 which is incorporated herein by reference for all purposes.

BACKGROUND OF THE INVENTION

Administrative, regulatory, legal, business, and other requirements may prescribe standards based on information printed on product labels or other printed material. Gathering and storing information on product labels often requires manually reading product labels and typing or writing what was read, which is a labor-intensive task. It would be useful to be able to reduce the errors and improve efficiency on this manual task.

BRIEF DESCRIPTION OF THE DRAWINGS

Various embodiments of the invention are disclosed in the following detailed description and the accompanying drawings.

FIG. 6A is nutrition data scan verification interface.

FIG. 6B is an ingredients data scan verification interface.

DETAILED DESCRIPTION

Figure 1:
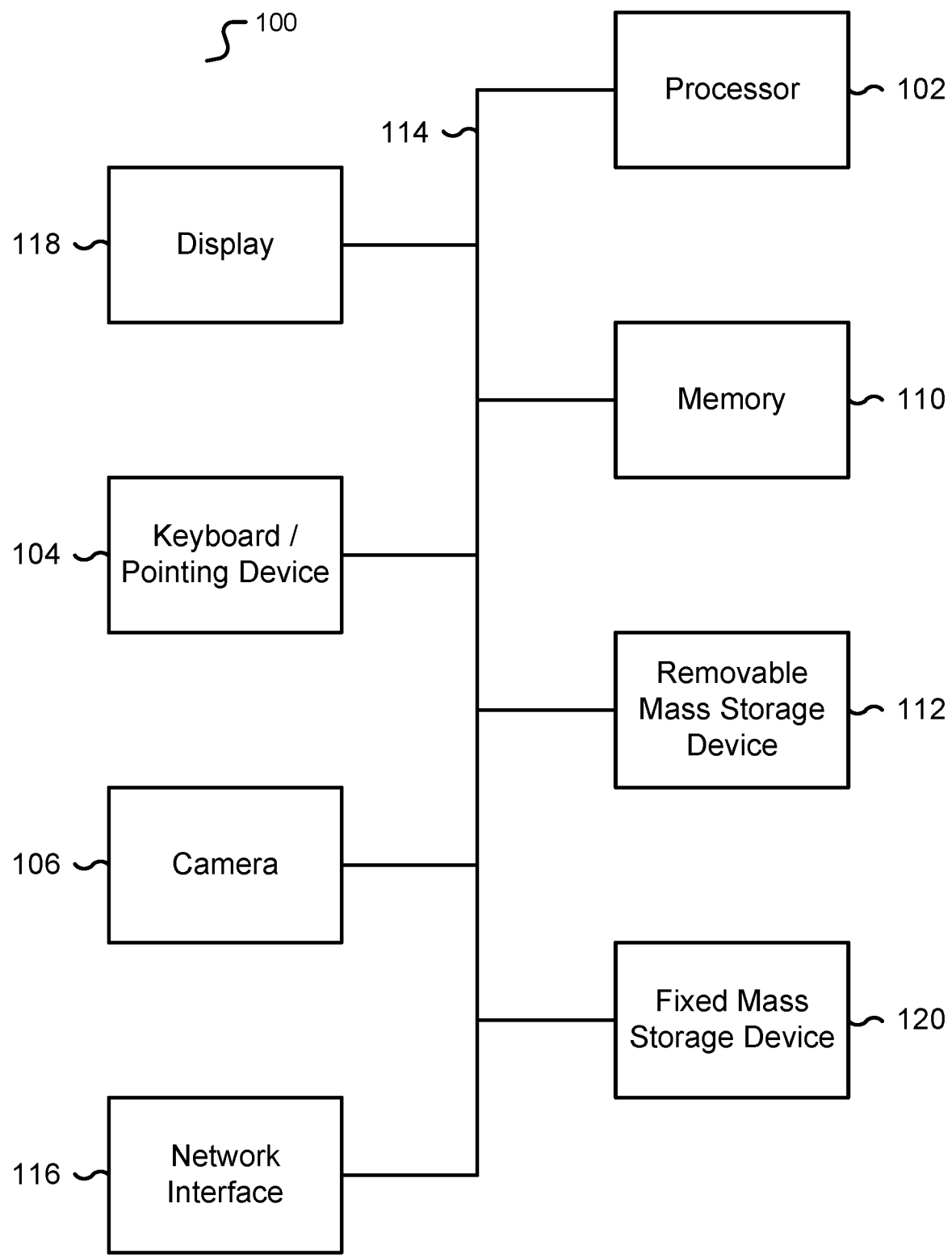
FIG. 1 is a functional diagram illustrating a programmed computer/server system for scanning labels to extract and store structured information in accordance with some embodiments.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Extracting data from product labels or other printed material is disclosed. In one embodiment, product labels conform to a standard that may be leveraged during the extraction. In one embodiment, information, such as the nutritional facts from a product's packaging, is extracted from a label or other printed material. For example, nutritional facts, allergy warnings, dosage information, drug interactions, or other information typically printed on a label or directly on a product or other article are extracted and stored in a table, database, or other structured/semi-structured data store.

While various example embodiments described herein involve solutions to extract information from US nutritional labels, without limitation similar techniques are employed in other contexts and embodiments to extract information other than nutritional information and/or are used to extract information from printed material other than product labels.

In one embodiment, nutritional information is extracted, for example serving size; calories; grams of fat, sugar, protein, or other nutrients; and percentage of daily allowance or other information. Guidelines for nutritional labels may conform to a standard, for example those published by government agencies, such as the U.S. Food & Drug Administration, who publishes information about their standard at https://www.fda.gov/food/nutrition-education-resources-materials/how-understand-and-use-nutrition-facts-label.

Extracting nutritional information from product labels may be an improvement, for example, for school districts who serve food to students from a wide range of vendors across the United States. Some school districts are required by law to keep a history of products and nutritional facts served to students. Traditionally, one approach requires school workers to manually read nutritional information from products and keep a history book up to date. A problem with this approach is that it does not yield satisfactory results as the data may be error-prone, incomplete, out of date, and/or costly to gather and maintain.

By contrast, with the standard product label, for example an FDA-compliant nutritional label, information that may be extracted using the disclosed includes:

The list of macronutrients and their values in grams. Currently one FDA standard includes total fat, saturated fat, trans fat, cholesterol, sodium, total carbohydrate, dietary fiber, total sugars, added sugars, and protein as example macronutrients;

Calories;

Serving Size;

List of ingredients;

Allergens; and/or

Micronutrients and their values in micrograms, milligrams, or IU.

Currently one FDA standard includes Vitamin D, Calcium, Iron, and Potassium as example micronutrients, and has also included Vitamin A and Vitamin C historically.

User problems that the disclosed solve comprise, for example:
- A user should be able to see an app to add nutrition data for any product more easily;
- A user should be able to search for any items that is in a data store to add nutrition data to it;
- A user should be able to see steps of scanning nutrition data to add nutrition data to the data store;
- A user should be able to start scanning by pointing the camera on a Nutrition Facts label and keep pressing scan so that the progress bar keeps progressing and/or get other forms of coaching on the scan, to extract a Nutrition Facts label data;
- A user scanning a Nutrition Facts label already should be able to start scanning ingredient data and keep pressing scan so that the progress bar on top keeps progressing and/or get other forms of coaching on the scan, to extract ingredients;
- A user who scanned a Nutrition Facts label and ingredients list should be able to see the results of scanned nutrition data in order to make a decision to submit this to a data store, cancel, or restart the process; and
- A user of a school district portal should be able see the nutrition data submitted through the mobile app in order to approve and/or fix any issues.

FIG. 1 is a functional diagram illustrating a programmed computer/server system for scanning labels to extract and store structured information in accordance with some embodiments. As shown, FIG. 1 provides a functional diagram of a general purpose computer system programmed to scan labels to extract and store structured information in accordance with some embodiments. An example of such a system includes a mobile phone, a tablet, a laptop computer, and a desktop computer. As will be apparent, other computer system architectures and configurations can be used for scanning labels to extract and store structured information.

Computer system (100), which includes various subsystems as described below, includes at least one microprocessor subsystem, also referred to as a processor or a central processing unit ("CPU") (102). For example, processor (102) can be implemented by a single-chip processor or by multiple cores and/or processors. In some embodiments, processor (102) is a general purpose digital processor that controls the operation of the computer system (100). Using instructions retrieved from memory (110), the processor (102) controls the reception and manipulation of input data, and the output and display of data on output devices, for example display and graphics processing unit (GPU) (118).

Processor (102) is coupled bi-directionally with memory (110), which can include a first primary storage, typically a random-access memory ("RAM"), and a second primary storage area, typically a read-only memory ("ROM"). As is well known in the art, primary storage can be used as a general storage area and as scratch-pad memory, and can also be used to store input data and processed data. Primary storage can also store programming instructions and data, in the form of data objects and text objects, in addition to other data and instructions for processes operating on processor (102). Also as well known in the art, primary storage typically includes basic operating instructions, program code, data and objects used by the processor (102) to perform its functions, for example programmed instructions. For example, primary storage devices (110) can include any suitable computer-readable storage media, described below, depending on whether, for example, data access needs to be bi-directional or uni-directional. For example, processor (102) can also directly and very rapidly retrieve and store frequently needed data in a cache memory, not shown. The processor (102) may also include a coprocessor (not shown) as a supplemental processing component to aid the processor and/or memory (110).

A removable mass storage device (112) provides additional data storage capacity for the computer system (100), and is coupled either bi-directionally (read/write) or uni-directionally (read only) to processor (102). For example, storage (112) can also include computer-readable media such as flash memory, portable mass storage devices, holographic storage devices, magnetic devices, magneto-optical devices, optical devices, and other storage devices. A fixed mass storage (120) can also, for example, provide additional data storage capacity. One example of mass storage (120) is an eMMC or microSD device. In one embodiment, mass storage (120) is a solid-state drive connected by a bus (114). Mass storage (112), (120) generally store additional programming instructions, data, and the like that typically are not in active use by the processor (102). It will be appreciated that the information retained within mass storage (112), (120) can be incorporated, if needed, in standard fashion as part of primary storage (110), for example RAM, as virtual memory.

In addition to providing processor (102) access to storage subsystems, bus (114) can be used to provide access to other subsystems and devices as well. As shown, these can include a display monitor (118), a communication interface (116), a touchscreen/virtual/physical keyboard (104), and one or more auxiliary input/output devices (104) including an audio interface, a sound card, microphone, audio port, audio recording device, audio card, speakers, a touch (or pointing) device, and/or other subsystems as needed. Besides a touch screen and/or capacitive touch interface, the auxiliary device (104) can be a mouse, stylus, track ball, or tablet, and is useful for interacting with a graphical user interface.

Client computer (100) may also include a camera (106) capable of video and/or image capture. For example, without limitation a camera (106) may be a front-facing camera, a rear-facing camera, a high definition camera, a multi-mega pixel camera, an infrared camera, a dual-camera system, a triple-camera system, a webcam, a conference camera, a video camera, an ultra-wide camera, a wide camera, and a telephoto camera.

The communication interface (116) allows processor (102) to be coupled to another computer, computer network, or telecommunications network using a network connection as shown. For example, through the communication interface (116), the processor (102) can receive information, for example data objects or program instructions, from another network, or output information to another network in the course of performing method/process steps. Information, often represented as a sequence of instructions to be executed on a processor, can be received from and outputted to another network. An interface card or similar device and appropriate software implemented by, for example executed/performed on, processor (102) can be used to connect the computer system (100) to an external network and transfer data according to standard protocols. For example, various process embodiments disclosed herein can be executed on processor (102), or can be performed across a network such as the Internet, intranet networks, or local area networks, in conjunction with a remote processor that shares a portion of the processing. Throughout this specification "network" refers to any interconnection between computer components including the Internet, Bluetooth, WiFi, 3G, 4G, 4GLTE, 5G, GSM, Ethernet, intranet, local-area network ("LAN"), home-area network ("HAN"), serial connection, parallel connection, wide-area network ("WAN"), Fibre Channel, PCI/PCI-X, AGP, VLbus, PCI Express, Expresscard, Infiniband, ACCESS.bus, Wireless LAN, HomePNA, Optical Fibre, G.hn, infrared network, satellite network, microwave network, cellular network, virtual private network ("VPN"), Universal Serial Bus ("USB"), FireWire, Serial ATA, 1-Wire, UNI/O, or any form of connecting homogenous, heterogeneous systems and/or groups of systems together. Additional mass storage devices, not shown, can also be connected to processor (102) through communication interface (116).

An auxiliary I/O device interface, not shown, can be used in conjunction with computer system (100). The auxiliary I/O device interface can include general and customized interfaces that allow the processor (102) to send and, more typically, receive data from other devices such as microphones, touch-sensitive displays, transducer card readers, tape readers, voice or handwriting recognizers, biometrics readers, cameras, portable mass storage devices, and other computers.

In addition, various embodiments disclosed herein further relate to computer storage products with a computer readable medium that includes program code for performing various computer-implemented operations. The computer-readable medium is any data storage device that can store data which can thereafter be read by a computer system. Examples of computer-readable media include, but are not limited to, all the media mentioned above: flash media such as NAND flash, eMMC, SD, compact flash; magnetic media such as hard disks, floppy disks, and magnetic tape; optical media such as CD-ROM disks; magneto-optical media such as optical disks; and specially configured hardware devices such as application-specific integrated circuits ("ASIC"s), programmable logic devices ("PLD"s), and ROM and RAM devices. Examples of program code include both machine code, as produced, for example, by a compiler, or files containing higher level code, for example a script, that can be executed using an interpreter.

The computer/server system shown in FIG. 1 is but an example of a computer system suitable for use with the various embodiments disclosed herein. Other computer systems suitable for such use can include additional or fewer subsystems. In addition, bus (114) is illustrative of any interconnection scheme serving to link the subsystems. Other computer architectures having different configurations of subsystems can also be utilized.

Figure 2:
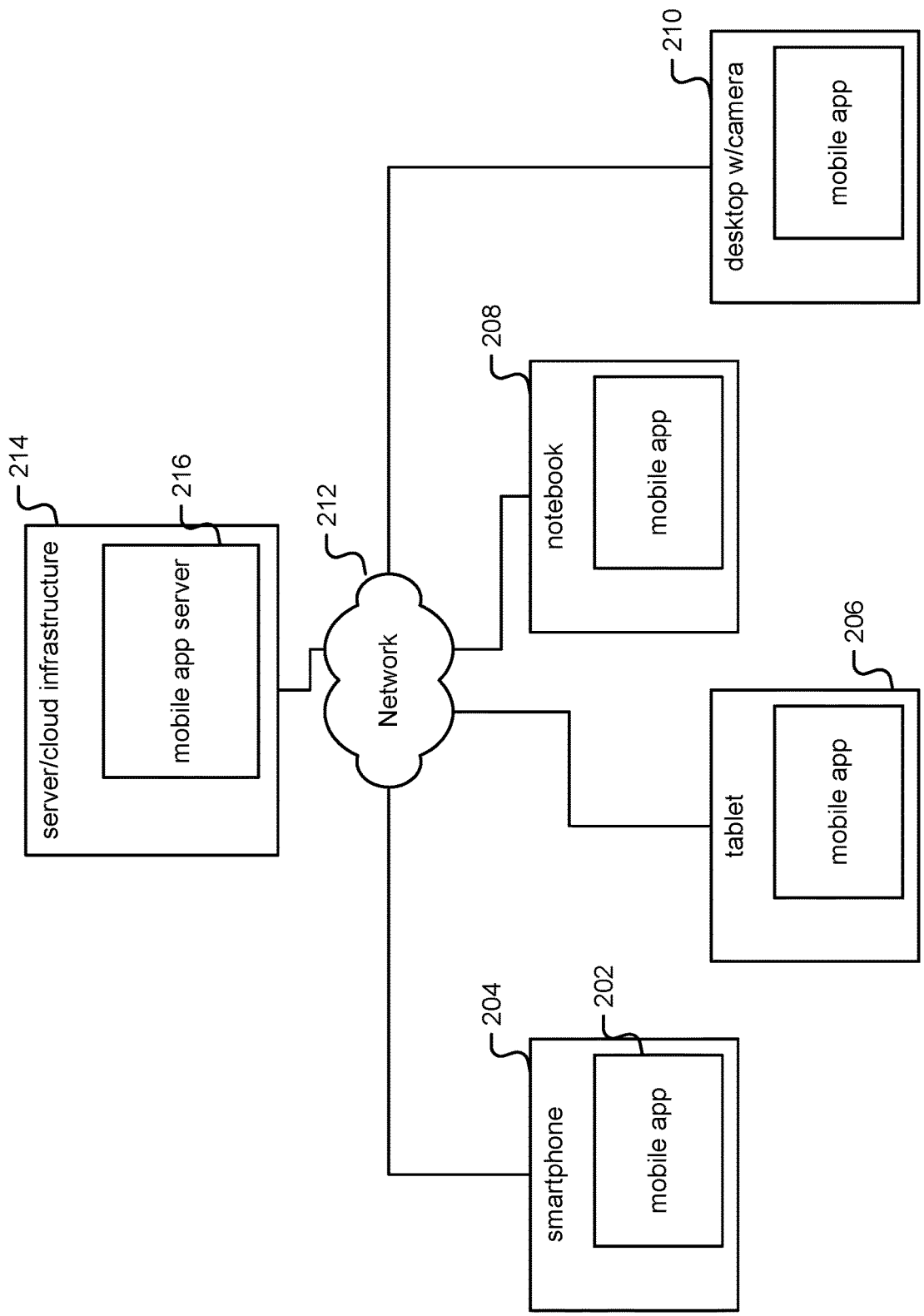
FIG. 2 is a block diagram illustrating an embodiment of a system for scanning labels to extract and store structured information.

FIG. 2 is a block diagram illustrating an embodiment of a system for scanning labels to extract and store structured information. Mobile app (202) is run locally/virtually/remotely on a client computer with a camera. Examples without limitation of said client computer include a smartphone (204), tablet (206), notebook (208), and/or desktop computer (210). For example, operating systems for client computer (204)/(206)/(208)/(210) may include iOS, Android, ChromeOS, Windows, Mac OS X, Linux, and UNIX. For example, browsers that may run on client computer (204)/(206)/(208)/(210) may include Safari, Chrome, Firefox, Edge, and Opera.

Client computer (204)/(206)/(208)/(210) is coupled via a network (212), such as the Internet, to a server/cloud infrastructure (214), where a mobile app server (216) is being run locally/virtually/remotely. For example, the server may be a bare metal server, a virtual server, dedicated on-premises hardware such as in-office computing and/or datacenter computing; and off-premises hardware such as cloud infrastructure including AWS ("Amazon Web Services), Microsoft Azure, IBM BlueMix, and/or GCP ("Google Cloud Platform").

Figure 3C:
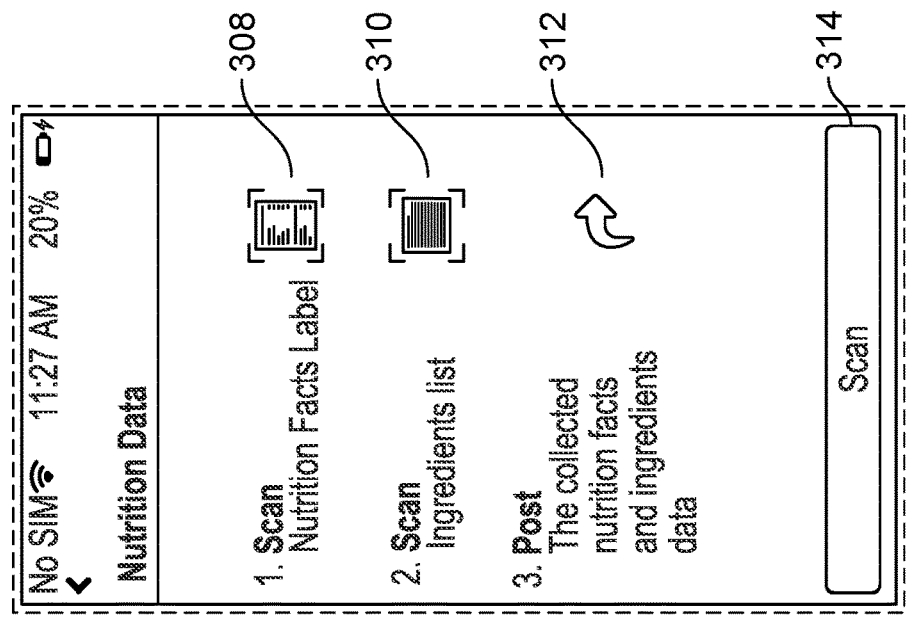
FIG. 3C is a nutrition data interface.
Figure 3B:
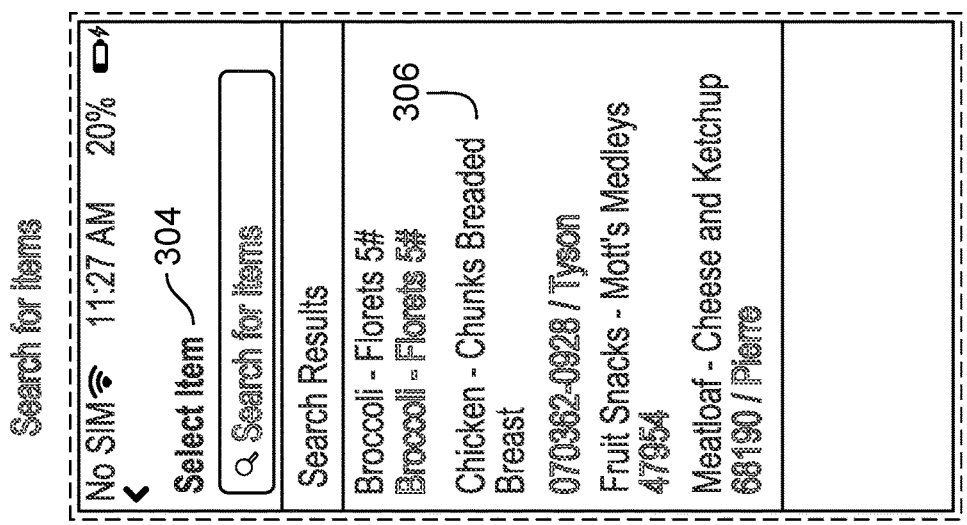
FIG. 3B is an item selection interface.
Figure 3A:
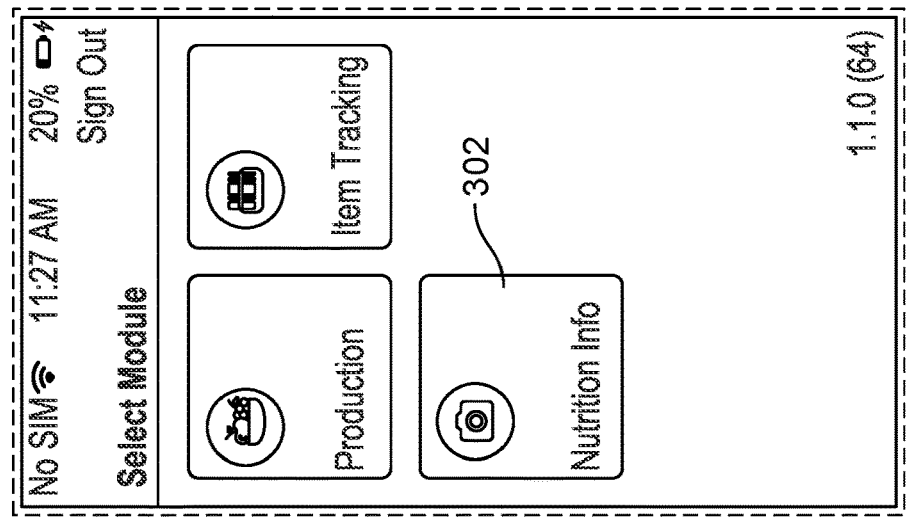
FIG. 3A is a module selection interface.

FIGS. 3A, 3B, and 3C illustrate an embodiment of a user flow for scanning labels to extract and store structured information. In one embodiment, the illustrations in FIGS. 3A, 3B, and 3C are screenshots/storyboards of a user interface on client computer (204) in FIG. 2.

FIG. 3A is a module selection interface. A user may choose to capture "Nutrition Info" (302) or do other tasks such as Production recipes, or Item Tracking. FIG. 3B is an item selection interface. After choosing Nutrition Info (302) in FIG. 3A, the user is asked to select an item (304) such as chicken (306) which may include an item number, such as 070362-0928, and/or other classification/tag words, like a manufacturer such as Tyson.

FIG. 3C is a nutrition data interface. A user, after selecting an item (304) in FIG. 3B, then is guided through a multi-step workflow including using camera (106) for FIG. 1 to scan a Nutrition Facts label (308), scan an ingredients list (310), and post the collected Nutrition Facts and ingredients data (312). A user may then commence scanning by asserting a "scan" interface element (314).

Figure 4:
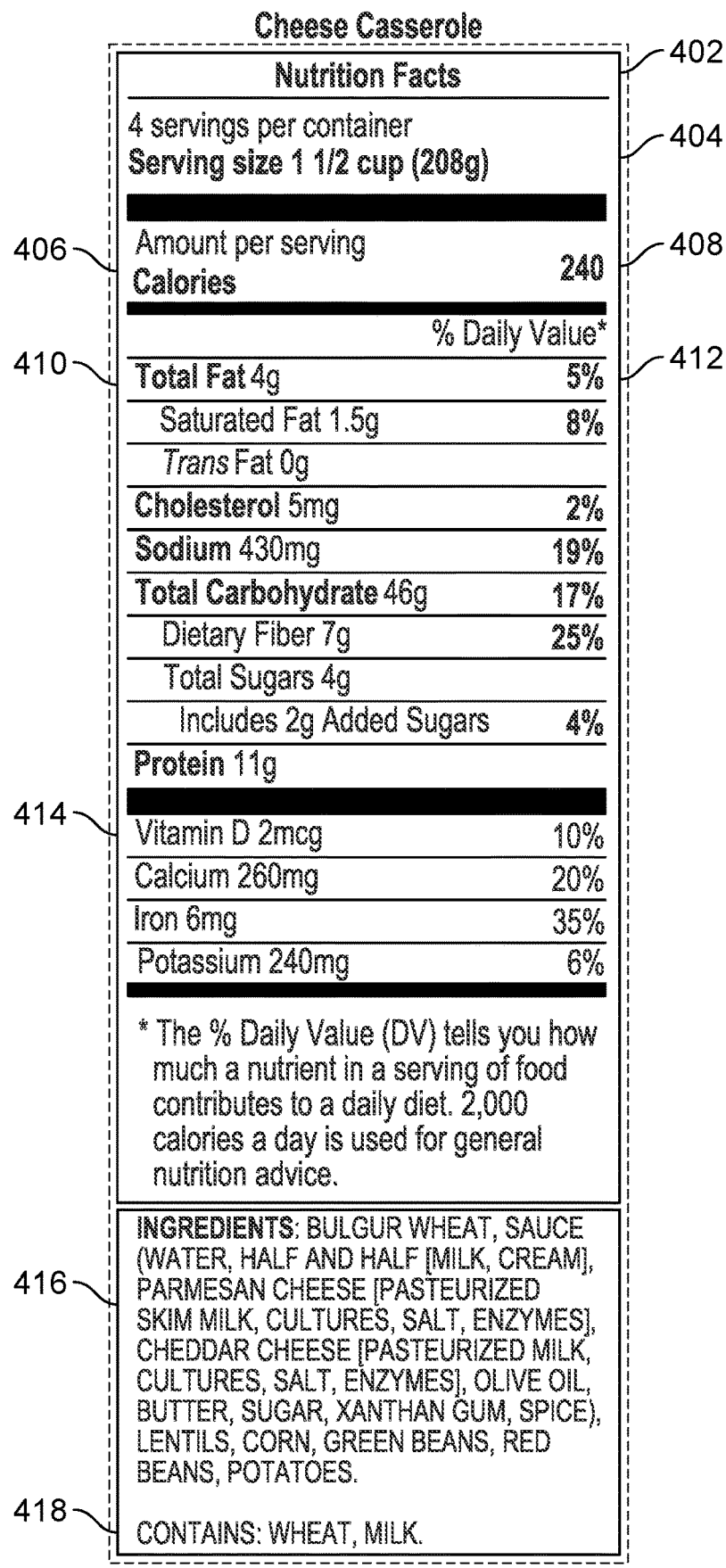
FIG. 4 is an example illustration of a Nutrition Facts label and ingredients list.

The Nutrition Facts label. In many countries, consumer packaged foods and beverages are required by law to have a consistent and standard format for labels, for example without limitation in the United States the FDA (Food and Drug Administration) requires a "Nutrition Facts" label and an ingredients list. FIG. 4 is an example illustration of a Nutrition Facts label and ingredients list. The example of FIG. 4 is a reproduction from the FDA web site at https://www.accessdata.fda.gov/scripts/InteractiveNutritionFacts-Label for a representative food item called here a Cheese Casserole.

The Nutrition Facts label (402) is governed in the United States by 21 CFR Part 101 and conforms to a standard requirement for typeface legibility for example Helvetica is a common legible choice, legal serving sizes (404), bold-faced type and/or regular type for specific sections such as the word Calories (406), and type size/font size for specific sections such as the calories value (408). Another example of a standards requirement is that of using black typeface on white background, rather than permitting other colors and/or a translucent background, to enhance legibility.

The Nutrition Facts label (402) has a list of macronutrients (410) including total fat, saturated fat, trans fat, cholesterol, sodium, total carbohydrate, dietary fiber, total sugars, added sugars, and protein. Each value of macronutrient is governed by "rounding rules" in terms of what are valid numbers to round towards in communicating the information, for example it is not legal to have 14.3 g as a value of Total Fat. Several macronutrients also have a quasi-redundant piece of information in terms of the % Daily Value (412), a percentage showing how much a nutrient in a serving of the labeled food contributes to a typical 2,000 calorie daily diet. For example, 4 g of Total Fat contributes 5% towards a typical 2,000 calorie daily diet value of 78 g of Total Fats.

Most Nutrition Facts labels also include micronutrients (414) such as Vitamin D, Calcium, Iron, Potassium, Vitamin A, and Vitamin C, along with their respective % Daily Value. The standard for micronutrients (414) is to report values in mg (milligrams), mcg (micrograms), and/or IU (international units) depending on the particular micronutrient.

The FDA also governs the listing of ingredients (416), including what food and beverage standards of identity may be used, for example "butter" according to 7 CFR § 58.345 only refers to a specific food item containing primarily milk fat and not, for example, almond milk or vegetable oil. Thus, there are a restricted number of ways to refer to a food item while complying to FDA standards. The FDA also governs the listing of allergens (418), in the number of major allergens, which allergen keywords for example milk, eggs, fish, shellfish, tree nuts, peanuts, wheat, and soybeans, and how to refer to them, for example either after keyword "contains" or less commonly in parentheses after each ingredient.

Any person of ordinary skill in the art recognizes that without limitation, herein are specific examples for the United States that are easily adapted for other countries that may have labeling requirements such as Australia and New Zealand, Brazil, Canada, China, the European Union, Hong Kong, India, Japan, Mexico, Russia, and the United Kingdom.

Figure 5B:
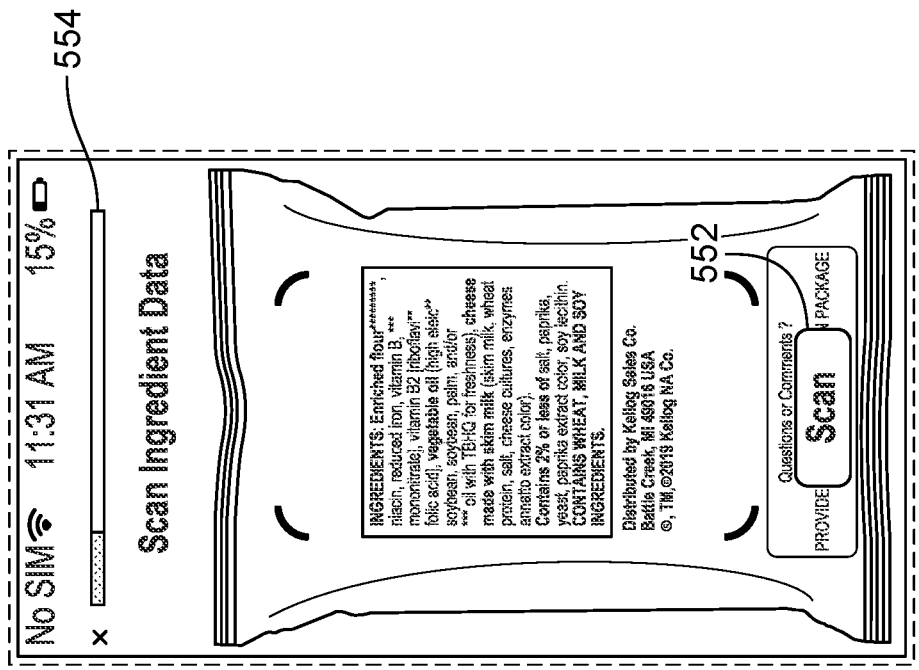
FIG. 5B is an ingredients data scanning interface.
Figure 5A:
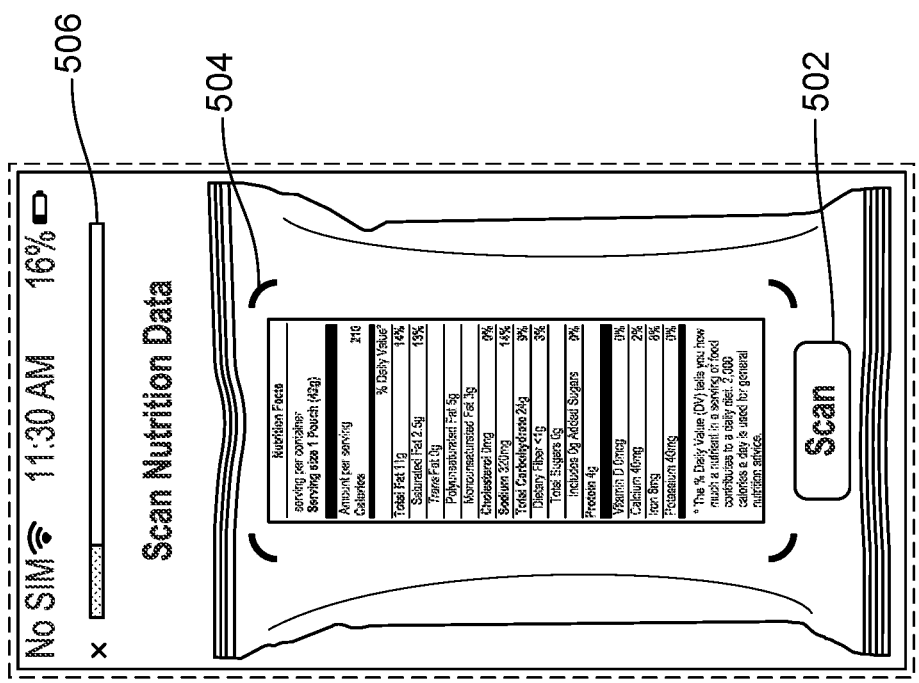
FIG. 5A is a nutrition data scanning interface.

FIGS. 5A and 5B are example illustrations of a scanning session. A user may see similar interfaces when asserting "scan" (314) in a nutrition data section of FIG. 3C. In one embodiment, Optical Character Recognition (OCR) analysis is used to extract text from images. Examples of OCR tools that may be used include Channel, an iOS Mobile App module, and/or libraries such as Firebase iOS SDK (ML Kit OCR API), Symmetric Delete spelling correction for .Net, and SymSpell.

In one embodiment, OCR frame preprocessing is used: frames are analyzed as they are being captured by a camera (106) to quickly detect whether the OCR-recognized and parsed text contains keywords such as "Nutrition", "Ingredients", or "Calories" (406). If those keywords are detected, it is concluded that the camera is pointing at a Nutritional Facts label.

Products with curved surfaces pose a challenge because the entire nutritional label is not visible in one frame, and many foods are found with packages with curved surfaces. In one embodiment, a solution to this challenge is to extract product label data from a live camera feed. During the live camera feed, frames are processed one by one.

The results of the extraction may then be aggregated by nutrient (or other information) type. Text blocks which include specific keywords such as "Ingredients" or "Calories", or match regular expressions for servings, or contextual rounding rules-based values are extracted.

FIG. 5A is a nutrition data scanning interface. As described in section (308) of FIG. 3C, the user may scan a Nutrition Facts label by asserting a "scan" interface element (502) and keeping a video stream from camera (106) in FIG. 1 trained on a physical Nutrition Facts label within the guidebars (504) and holding the camera (106) steady. A progress bar (506) may advance as the stream is processed and it is determined whether multiple frames and/or angles are required to adjust for lighting, glare, warping, shake, and so forth. Not shown in FIG. 5A, there may be additional "coaching" interface elements to guide a user to reposition a camera in a different translational and/or rotational way to improve the nutrition data scan.

In one embodiment, once processing starts, a camera frame is captured and converted into an image. The image is input to OCR analysis to get raw text results. Extracted text blocks that comprise specific keywords (e.g., "Ingredients", "Calories") or matches regular expressions for servings are used to provide structural context within the structure of a valid Nutrition Facts label.

Quantity for serving size and for specific macronutrient and/or micronutrient data is then analyzed, for example Fat being 1 g or Sodium being 730 mg. Again, the structural context of a valid Nutrition Facts label may be leveraged to bias rejection, for example an illegal value of Sodium being 7.30 mg if a competing analysis shows a valid value of Sodium being 730 mg. All quantity results are saved, and a confidence score for each result is assessed based on structural context and/or how many times each result appears for a specific nutrient in each of the camera frames.

The reported serving and nutrition information may then be presented, for example a reported serving quantity may be that the highest confidence score, and a reported nutrition name and quantity may be that with the highest confidence score/pair. For serving size, regular expressions may be used to find text that contains serving info, for example "1 pack (21 g)". In one embodiment, a regular expression used for serving size is "\(\d+\.*\d*\s{0,1}?m{0,1}?(g\w*|L\w*)(\)|\/)".

In one embodiment, images (for example the one shown in FIG. 5A) and/or a sampled subset of them are sent to a remote server (214) in FIG. 2 and processed using OCR analysis, for example the steps above, to extract nutritional or other semantic information. In an alternate embodiment, images are scanned and OCR analysis happens in the same device, a client (204)/(206)/(208)/(210). Extracted information may be displayed via a display user interface at a client (204)/(206)/(208)/(210), and/or stored locally at the client device (204)/(206)/(208)/(210) or at a backend server (214).

FIG. 5B is an ingredients data scanning interface. As described in section (310) of FIG. 3C, the user may scan a ingredients list by asserting a "scan" interface element (552) and keeping a video stream from camera (106) in FIG. 1 trained on a physical ingredients list in the guidebars (504) and holding the camera (106) steady. A progress bar (554) may advance as the stream is processed and it is determined whether multiple frames and/or angles are required to adjust for lighting, glare, warping, shake, and so forth. Not shown in FIG. 5B, there may be additional "coaching" interface elements to guide a user to reposition a camera in a different translational and/or rotational way to improve the ingredients data scan.

In one embodiment, once processing starts, a camera frame is captured and converted into an image. The image is input to OCR analysis to get raw text results. One analysis is to correct words in the text blocks based on a custom-built ingredients dictionary which includes modern food ingredients and/or a domain-aware dictionary. For example, the FDA standards of identity are dictionary entries in the dictionary, for example "butter". Other non-ingredients entries in a domain-aware dictionary are allergens which are typically referred to by keywords "milk", "eggs", "fish", "shellfish", "tree nuts", "peanuts", "wheat", and "soybeans", after keyword "contains" or within parentheses.

In one embodiment, once words are corrected, text blocks are split into segments, such that each segment represents one ingredient. Segments are saved a count is maintained for how many times each have appeared. If valid ingredients data has been found, a progress indicator (554) is shown to increase progress. The steps in the paragraph herein are repeated until all ingredient information has been processed, at which point the progress indicator (554) reaches complete. In a results table, ingredients information may be presented, for example the ingredient name and how many times that ingredient has been found, or a frequency count.

In one embodiment, images (for example the one shown in FIG. 5B) and/or a sampled subset of them are sent to a remote server (214) in FIG. 2 and processed using OCR analysis, for example the steps above, to extract ingredients or other semantic information. In an alternate embodiment, images are scanned and OCR analysis happens in the same device, a client (204)/(206)/(208)/(210). Extracted information may be displayed via a display user interface at a client (204)/(206)/(208)/(210), and/or stored locally at the client device (204)/(206)/(208)/(210) or at a backend server (214).

In one embodiment, a set of keywords to directly process Nutrition Facts label information and/or ingredients information, or indirectly process, for example provide physical layout information/context and/or hints include:

"Nutrition Facts"
"Servings per container"
"Serving size"
"Calories"
"Amount per serving"
Macronutrients:
  "Fat Calories"
  "Total Fat"
  "Saturated Fat"
  "Trans Fat"
  "Unsaturated Fat"
  "Polyunsaturated Fat"
  "Monounsaturated Fat"
  "Cholesterol"
  "Sodium"
  "Total Carbohydrate"
  "Dietary Fiber"
  "Soluble Fiber"
  "Total Fiber"
  "Total Sugars"
  "Added Sugars"
  "Protein"
Micronutrients:
  Vitamin A
  Vitamin C
  Vitamin D
  Calcium
  Iron
  Potassium
"The % Daily Value (DV) tells you how much a nutrient in a serving of food contributes to a daily diet. 2,000 calories a day is used for general nutrition advice."
Ingredients:
  "Ingredients"
  <names of ingredients>
  <names of standards of identity>
Allergens:
  "Contains"
  "Milk"
  "Eggs"
  "Fish"
  "Shellfish"
  "Tree Nuts"
  "Peanuts"
  "Wheat"
  "Soybeans"

In one embodiment, one or more of the following techniques are used to increase the effectiveness of the OCR analysis:

1. Naive dictionary text matching. For example, text is matched against a dictionary of keywords such as those described above and/or found on Nutrition Facts labels and/or list of ingredients;
2. Levenshtein Algorithm. For example, in the event output text does not match exactly with expected words/keywords/entries, for example "C4lor1es" instead of "Calories", the Levenshtein distance algorithm may be used to match results with expected text; and
3. Auto Correction:
   In one embodiment, autocorrection of output uses a third-party library such as SymSpell which works using a dictionary of English words and via frequency counts. The word frequency, for example across a plurality of image frames, determines at least in part the likelihood of a correction for a specific input; and
   In one embodiment, an initial version of an nutrition/ingredients dictionary is built and bundled in a mobile app (202) in FIG. 2. This dictionary is maintained and enhanced by backend processes and/or human curators using for example a server (214), and mobile app (202) is subsequently updated to download a latest version of the dictionary.

Confidence Score. In one embodiment, due to the nature of the live feed used to perform OCR on successive image frames taken at different angles, multiple readings of the same nutrient may happen. For example, for "Total Fat", it is possible that multiple different values are read: "19 g", "1 g", and "9 g".

In one embodiment, in order to provide the user with the best prediction, readings from multiple images are aggregated and evaluated across images, wherein only the reading with the highest frequency and/or other measure of confidence is reported.

In the example above, for example, for "Total Fat" multiple readings may be obtained from different frames (images) comprising a live feed, such as:
  19 g×5
  9 g×1
  1 g×1
The value 19 g may be selected, in this example, because its frequency is the highest at 71%, which is 5/7×100%. In the case that readings have similar frequencies, the latest may be selected.

In one embodiment, preprocessing and/or other processing is used to improve the confidence score and/or OCR analysis. For instance, for the "Total Fat" example above the % Daily Value may also be scanned at the end of the Total Fat row for a "% Daily Value correlation" for nutrients with a % Daily Value, so that if entries are:
  a) 19 g 24%
  b) 19 g 2.4%
  c) 19 g 24%
  d) 19 g 24%
  e) 9 g 24%
  f) 1 g 24%
  g) 19 g 24%
then a computation of % Daily Value may be used to validate entries (a), (c), (d), and (g) of 19 g Total Fat with a 24% Daily Value as 19 g÷78 g=24%, and/or invalidate entries (b), (e), and (f) as 19 g of Total Fat does not correlate with 2.4% Daily Value, nor does 9 g of Total Fat or 1 g of Total Fat correlate with 24% Daily Value. After a % Daily Value correlation preprocessing, the surviving results may then use the confidence score technique described above. The % Daily Value correlation is referred to herein as an example of a structural context element.

In one embodiment, another structural context element is correlation with a legal serving size, for example whether an ice cream has a serving size of ⅔ cups may validate the serving size OCE analysis. Another structural context element is validating typefaces, for example Helvetica, that are considered legible by the FDA. A similar structural context element is validating text that has been bold-face for a keyword like "Calories". A similar structural context element is correlating type size/font size for a specific section such as the calories value (408) in FIG. 4, where calories should be of a larger proportional size than other type sizes on the label.

In one embodiment, another structural context element is using FDA rounding rules to validate numbers that use proper rounding rules such as 14 g of Total Fat but invalidate/reject numbers that do not, such as 14.3 g of Total Fat. Another structural context element is validating labels that are black typeface on white background, and invalidating entries with other colors and/or a translucent background.

In one embodiment, dimensional order is used to improve OCR analysis and/or better assess a confidence score. Dimensional order includes finding lines such as the grid typically used for Nutrition Facts labels, or using the order of raw text output, for example Fat is before Carbohydrates which is before Protein on a Nutrition Facts label. In one embodiment, bounding box analysis is used to improve OCR analysis and/or better assess a confidence score. Bounding box analysis includes recognizing small rectangles on each line and/or subline, and using a bounding box to limit the OCR analysis within so that, for example, glare and/or noise is ignored outside of a bounding box.

Most Nutrition Facts labels also include micronutrients (414) such as Vitamin D, Calcium, Iron, Potassium, Vitamin A, and Vitamin C, along with their respective % Daily Value. The standard for micronutrients (414) is to report values in mg (milligrams), mcg (micrograms), and/or IU (international units) depending on the particular micronutrient.

The FDA also governs the listing of ingredients (416), including what food and beverage standards of identity may be used, for example "butter" according to 7 CFR § 58.345 only refers to a specific food item containing primarily milk fat and not, for example, almond milk or vegetable oil. Thus, there are a restricted number of ways to refer to a food item while complying to FDA standards. The FDA also governs the listing of allergens (418), in the number of major allergens, which allergen keywords for example milk, eggs, fish, shellfish, tree nuts, peanuts, wheat, and soybeans, and how to refer to them, for example either after keyword "contains" or less commonly in parentheses after each ingredient.

FIGS. 6A and 6B are example illustrations of a posting session. A user may see similar interfaces after asserting "scan" (314) in a nutrition data section of FIG. 3C and going through the camera workflows of FIGS. 5A and 5B.

FIG. 6A is nutrition data scan verification interface. A user may now refer to the scanned and reported quantities for nutrition (602) and verify it physically matches with the Nutrition Facts label. FIG. 6B is an ingredients data scan verification interface. In one embodiment, FIG. 6B is contiguous with the nutrition data scan verification interface of FIG. 6A to be scrolled up or down between them. Ingredients may be reported (604) along with a frequency count and/or ordered list of the ingredient keyword (606). A "submit" interface element (608) may be asserted to submit the scanned data to a data store for storage and dissemination, for example to a school district database.

Figure 7:
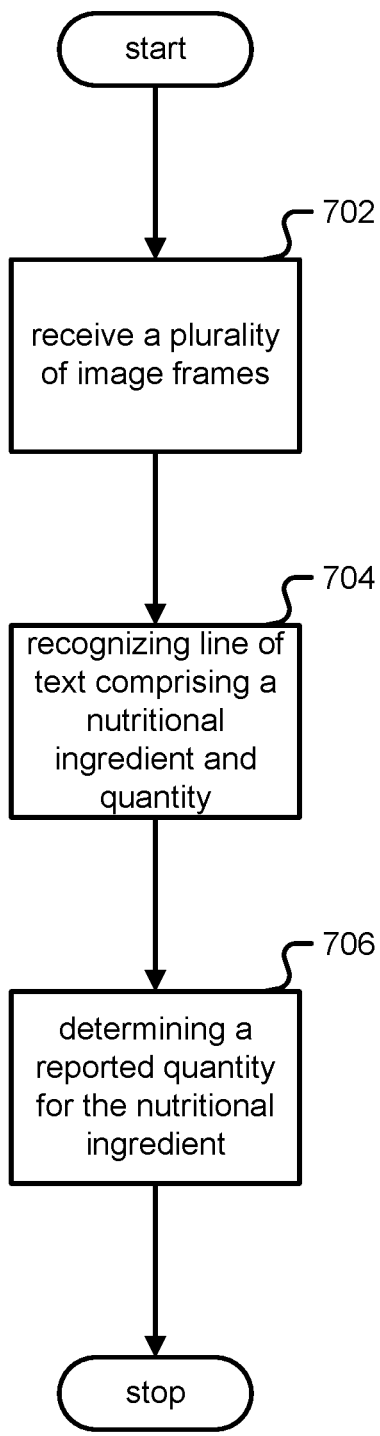
FIG. 7 is a flow chart illustrating an embodiment of a process for scanning labels to extract and store structured information.

FIG. 7 is a flow chart illustrating an embodiment of a process for scanning labels to extract and store structured information. In one embodiment, the process of FIG. 7 is carried out by a client computer (204), a server (214), or both which are shown in FIG. 2.

In step 702, a plurality of image frames is received. These image frames may be received from camera (106) in FIG. 1 via a video stream as shown for example in FIGS. 5A and 5B. In one embodiment, the plurality of image frames is from a video stream, for example a video stream of a food or beverage package.

In step 704, in each of at least a subset of the image frames a line of text comprising a nutritional ingredient and a corresponding frame-specific quantity is recognized. For example, a line of text may include the word "Calories" (406) and a corresponding quantity may be 240 (408) as shown in FIG. 4. In one embodiment, the nutritional element examples include: macronutrients, list of ingredients, calories, serving size, micronutrients, and allergens.

In one embodiment, recognizing comprises mapping a structural context element. The structural context element may be based on a standard, for example: an administrative standard, a regulatory standard, a legal standard, a business standard, and a de facto standard. The structural context element may include: color, number of colors, columnar format, typeface, type size, relative position on label, number of occurrences, and % Daily Value correlation.

In one embodiment, recognizing comprises using OCR analysis. The OCR analysis may include: naive dictionary text matching, Levenshtein algorithm, autocorrection, and regexp matching. The OCR analysis may also include % Daily Value validation and analysis based on rounding rules.

In one embodiment, OCR analysis is offloaded remotely to a server. The mobile client (204) may be configured to receive a server OCR analysis and to use the server OCR analysis. In one embodiment, a step not shown in FIG. 7 is a step to coach a user on repositioning the camera for a second plurality of image frames.

In step 706, a reported quantity for the nutritional ingredient is determined based at least in part on the respective corresponding frame-specific quantities. For example, if five frames each report 240 calories, the reported quantity for calories may be determined to be 240. In one embodiment, this step of determining comprises assessing a confidence score. The confidence score may be based at least in part on a dimensional order. The confidence score may be based at least in part on a bounding box analysis.

In one embodiment, a step not shown in FIG. 7 is the posting or transmitting of the reported quantity for the nutritional ingredient to a mobile app server and/or data store. In one embodiment, the server executes the process of FIG. 7 and the plurality of image frames are received from a mobile app client on client computer (204) of FIG. 2.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system, comprising:
a communication interface; and
a processor coupled to the communication interface and configured to:
 receive a video stream of a food or beverage package comprising a plurality of image frames;
 recognize in each of at least a subset of the image frames a line of text comprising a nutritional ingredient and a corresponding frame-specific quantity, wherein recognizing comprises mapping a structural context element based on a standard;

wherein the standard includes at least one of the following: an administrative standard, a regulatory standard, a legal standard, a business standard, and a de facto standard;

wherein the structural context element comprises an element associated with the standard based at least in part on one of following: color, number of colors, columnar format, typeface, type size, relative position on label, number of occurrences, rounding rules, keywords, serving size, standards of identity, and % Daily Value correlation;

preprocess the respective corresponding frame-specific quantities using the structural context element; and determine a reported quantity for the nutritional ingredient based at least in part on a statistical confidence score based at least in part on aggregation of the preprocessed frame-specific quantities.

2. The system of claim 1, wherein recognizing comprises using optical character recognition (OCR) analysis.

3. The system of claim 2, wherein OCR analysis comprises using at least one of the following: naive dictionary text matching, Levenshtein algorithm, autocorrection, and regexp matching.

4. The system of claim 2, wherein OCR analysis comprises using % Daily Value correlation and rounding rules.

5. The system of claim 1, wherein the processor is further configured to receive a server OCR analysis and wherein recognizing comprises using the server OCR analysis.

6. The system of claim 1, wherein determining comprises assessing a confidence score.

7. The system of claim 6, wherein the confidence score is based at least in part on a dimensional order.

8. The system of claim 6, wherein the confidence score is based at least in part on a bounding box analysis.

9. The system of claim 1, further comprising a camera.

10. The system of claim 9, wherein the processor is further configured to coach a user on repositioning the camera for a second plurality of image frames.

11. The system of claim 1, wherein the processor is further configured to transmit the reported quantity for the nutritional ingredient to a mobile app server.

12. The system of claim 1, wherein the nutritional element is at least one of: macronutrients, list of ingredients, calories, serving size, micronutrients, and allergens.

13. The system of claim 1, wherein the plurality of image frames is received from a mobile app client.

14. A method, comprising:

receiving a video stream of a food or beverage package comprising a plurality of image frames;

recognizing in each of at least a subset of the image frames a line of text comprising a nutritional ingredient and a corresponding frame-specific quantity, wherein recognizing comprises mapping a structural context element based on a standard;

wherein the standard includes at least one of the following: an administrative standard, a regulatory standard, a legal standard, a business standard, and a de facto standard;

wherein the structural context element comprises an element associated with the standard based at least in part on one of following: color, number of colors, columnar format, typeface, type size, relative position on label, number of occurrences, rounding rules, keywords, serving size, standards of identity, and % Daily Value correlation;

preprocessing the respective corresponding frame-specific quantities using the structural context element; and determining a reported quantity for the nutritional ingredient based at least in part on a statistical confidence score based at least in part on aggregation of the preprocessed frame-specific quantities.

15. A computer program product, the computer program product being embodied in a non-transitory computer readable storage medium and comprising computer instructions for:

receiving a video stream of a food or beverage package comprising a plurality of image frames;

recognizing in each of at least a subset of the image frames a line of text comprising a nutritional ingredient and a corresponding frame-specific quantity, wherein recognizing comprises mapping a structural context element based on a standard;

wherein the standard includes at least one of the following: an administrative standard, a regulatory standard, a legal standard, a business standard, and a de facto standard;

wherein the structural context element comprises an element associated with the standard based at least in part on one of following: color, number of colors, columnar format, typeface, type size, relative position on label, number of occurrences, rounding rules, keywords, serving size, standards of identity, and % Daily Value correlation;

preprocessing the respective corresponding frame-specific quantities using the structural context element; and determining a reported quantity for the nutritional ingredient based at least in part on a statistical confidence score based at least in part on aggregation of the preprocessed frame-specific quantities.

* * * * *